United States Patent [19]
Mukerji et al.

[11] Patent Number: 5,942,254
[45] Date of Patent: *Aug. 24, 1999

[54] PHOSPHORYLATED RECOMBINANT HUMAN β-CASEIN EXPRESSED IN A BACTERIAL SYSTEM

[75] Inventors: Pradip Mukerji, Gahanna; Jennifer Marie Thurmond, Columbus, both of Ohio; Lennart Hansson, Umeå, Sweden; Jeffrey Harris Baxter, Galena; Robert George Hards, Delaware, both of Ohio

[73] Assignee: Abbott Laboratories, Abbott Park, Ill.

[*] Notice: This patent issued on a continued prosecution application filed under 37 CFR 1.53(d), and is subject to the twenty year patent term provisions of 35 U.S.C. 154(a)(2).

[21] Appl. No.: 08/554,137

[22] Filed: Nov. 6, 1995

Related U.S. Application Data

[63] Continuation-in-part of application No. 08/395,239, Feb. 27, 1995, abandoned.

[51] Int. Cl.$^6$ .......................... A61K 35/20; A61K 38/17; A23C 9/15; A23J 1/20
[52] U.S. Cl. .......................... 424/535; 426/580; 530/350; 530/360; 530/832
[58] Field of Search ................................. 530/360, 350, 530/832; 435/320.1, 172.3, 194, 69.1; 536/23.5, 24.1, 23.2; 424/535; 426/580

[56] References Cited

FOREIGN PATENT DOCUMENTS

| | | |
|---|---|---|
| 2083521 | 10/1993 | Canada . |
| 0178863 | 4/1986 | European Pat. Off. . |
| 445097A3 | 2/1990 | European Pat. Off. . |
| 548012A1 | 6/1993 | European Pat. Off. . |
| WO91/06308 | 5/1991 | WIPO . |
| WO91/08675 | 6/1991 | WIPO . |
| WO9209698 | 6/1992 | WIPO . |
| WO93/04171 | 3/1993 | WIPO . |
| WO93/04172 | 3/1993 | WIPO . |
| WO94/06306 | 3/1994 | WIPO . |
| WO9413796 | 6/1994 | WIPO . |
| WO95/32727 | 12/1995 | WIPO . |
| WO95/32728 | 12/1995 | WIPO . |
| WO96/27018 | 9/1996 | WIPO . |
| WO97/17085 | 5/1997 | WIPO . |
| WO97/17449 | 5/1997 | WIPO . |

OTHER PUBLICATIONS

Chemical Abstracts, vol. 112, No. 19, May 7, 1990, p. 221 Jimenez–Flores, R. et al., "Expression of bovine Beta casein in *Saccharomyces cerevisiae* and characterization of the protein produced in vivo.".

309 Journal of Dairy Science (ADSA), 71, (1988) Oct., No. 10, Champaign, IL, USA. Jimeneze–Flores, R. et al., "Genetic engineering of the caseins to modify the behavior of milk during processing: A review".

Chemical Abstracts, vol. 120, No. 3, Jan. 17, 1994, Columbus, OH, US, Abstract 25819, Hansson, Lennart et al., "Expression of human milk.beta.–casein in *Escherichia coli* . . . ".

Adv. Exp. Med. Biol., vol. 310, 1991, pp. 167–171, C. Svanborg et al.: "Anti–Adhesive Molecules In Human Milk".

Micro. Pathog., vol. 8, No. 5, May 1990, pp. 315–323, G. Aniansson et al.: "Anti–Adhesive Activity of Human Casein Against *Streptococcus Pneumoniae* and *Haemophilus Influenzae*".

Biochemical and Biophysical Research Communications, vol. 203, No. 1, Aug. 30, 1994, pp. 225–230, Jeng et al., "Production of an Enzymatically Active E1 Component of Human Pyruvate Dehydrogenase Complex in *Escherichia coli*: Supporting Role of E1 Beta Subunit in E1 Activity".

Proceedings of the National Academy of Sciences, USA, vol. 91, Mar. 15, 1994, pp. 2767–2771, Shi et al., "Expression of Recombinant Human Casein Kinase II and Recombinant Heat Shock Protein 90 in *Excherichia coli* and Characterization of Their Interactions".

Groves et al., Archives of Biochemistry and Biophysics 140:47–51 (1970).

Greenberg et al., J. Biol. Chem. 259:5132–5138 (1984).

Hansson et al., Protein Expression and Purification 4:373–381 (1993).

*Primary Examiner*—Johnny F. Railey, II
*Attorney, Agent, or Firm*—Cheryl L. Becker

[57] ABSTRACT

The present invention provides a plasmid containing a promoter sequence, a nucleotide sequence encoding an exogenous protein, and a nucleotide sequence encoding an enzyme capable of modifying the exogenous protein. In a specific embodiment of the invention the encoded exogenous protein is human β-casein and the encoded enzyme is a human kinase capable of phosphorylating recombinant β-casein in a bacterial system. Phosphorylated recombinant human β-casein synthesized using the plasmid of the invention is shown to have the same bioactivity as native human β-casein.

13 Claims, 11 Drawing Sheets

1. LMW MARKER 5 ul
2. NATIVE HUMAN β-CASEIN 50 ng
3. HMS174 (DE3)pLysS      (pRJB-7) UNINDUCED LYSATE (UL)
4.    "          "         (pRJB-7) INDUCED LYSATE (IL)
5.    "          "         (pET 11d-CKIIβα) UL
6.    "          "         (pET 11d-CKIIβα) IL
7.    "          "         (pRJB-9) UL
8.    "          "         (pRJB-9) IL

UL= UNINDUCED LYSATE     IL= INDUCED LYSATE

1. LMW MARKER 5 ul
2. NATIVE β-CASEIN 1 ug
3. NATIVE β-CASEIN 2 ug
5. HMS174 (DE3)pLysS       (pET-11d-CK11 βα) INDUCED
6.      "              "       (pRJB-9) INDUCED
7.      "              "       (pRJB-7) INDUCED
8.      "              "       (pS637)  INDUCED
10. RECOMBINANT β-CASEIN 1 ug
11. RECOMBINANT β-CASEIN 2 ug

LANE 1: 5μl OF LMW MARKER (GIBCO BRL)
LANE 2: 50 ng OF NATIVE HUMAN β-CASEIN
LANE 3: LYSATE OF INDUCED HMS174(DE3)pLysS(pRJB-9)
LANE 4: LYSATE OF INDUCED HMS174(DE3)pLysS(pS637)
LANE 5: LYSATE OF INDUCED HMS174(DE3)pLysS(pET11d-CK11βα)
LANE 6: 50 ng OF RECOMBINANT HUMAN β-CASEIN

LANE 1: 5μl OF LMW MARKER (GIBCO BRL)
LANE 2: 1μg OF NATIVE HUMAN β-CASEIN
LANE 3: 500ng OF NATIVE HUMAN β-CASEIN
LANE 4: LYSATE OF INDUCED HMS174(DE3)pLysS(pRJB-9)
LANE 5: LYSATE OF INDUCED HMS174(DE3)pLysS(pS637)
LANE 6: LYSATE OF INDUCED HMS174(DE3)pLysS(pET11d-CKIIβα)
LANE 7: 1μg OF RECOMBINANT HUMAN β-CASEIN
LANE 8: 500ng OF RECOMBINANT HUMAN β-CASEIN

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
      (A) LENGTH:   31 base pairs
      (B) TYPE:  Nucleic acid
      (C) STRANDEDNESS:  Single
      (D) TOPOLOGY:   Linear (ii) MOLECULE TYPE:   DNA (xi) SEQUENCE DESCRIPTION: SEQ ID NO: 1:

CGCTGCAGCA TATGCGTGAA ACCATCGAAT C                              31

(2) INFORMATION FOR SEQ ID NO:2:

(i) SEQUENCE CHARACTERISTICS:
      (A) LENGTH:    61 base pairs

-continued

```
        (B) TYPE:  Nucleic acid
        (C) STRANDEDNESS:  Single
        (D) TOPOLOGY:  Linear (ii) MOLECULE TYPE:  DNA (xi) SEQUENCE DESCRIPTION: SEQ ID NO: 2:

CGGGATCCTG GTCCTCGTGT TTAACTTTTT CAACTTTCTG TTTGTATTCG GTGATCGATT        61

(2) INFORMATION FOR SEQ ID NO:3:

(i) SEQUENCE CHARACTERISTICS:
        (A) LENGTH:   18 base pairs
        (B) TYPE:  Nucleic acid
        (C) STRANDEDNESS:  Single
        (D) TOPOLOGY:  Linear (ii) MOLECULE TYPE:  DNA (xi) SEQUENCE DESCRIPTION: SEQ ID NO: 3:

TGTAAAACGA CGGCCAGT                                                     18

(2) INFORMATION FOR SEQ ID NO:4:

(i) SEQUENCE CHARACTERISTICS:
        (A) LENGTH:   21 base pairs
        (B) TYPE:  Nucleic acid
        (C) STRANDEDNESS:  Single
        (D) TOPOLOGY:  Linear (ii) MOLECULE TYPE:  DNA (xi) SEQUENCE DESCRIPTION: SEQ ID NO: 4:

GGGGATCCGT ACGCGTGAAA C                                                 21
```

PHOSPHORYLATED RECOMBINANT HUMAN β-CASEIN EXPRESSED IN A BACTERIAL SYSTEM

This application is a continuation-in-part of U.S. Ser. No. 08/395,239 filed on Feb. 27, 1995 now abandoned.

TECHNICAL FIELD

This invention relates to a novel method for producing modified recombinant proteins in a bacterial system. The method comprises preparing a single vector having a nucleotide sequence encoding an exogenous protein and an enzyme capable of modifying the protein in vivo, and expressing the vector in the host cell to produce a modified protein. An aspect of the invention relates to a single vector containing a promoter, followed by a protein encoding sequence, followed by an enzyme encoding sequence. Data are presented that show that the modified protein has the same activity as native human protein.

BACKGROUND OF THE INVENTION

It is generally recognized that human milk is the best nutritional source for human infants. Human milk is not only an ideal source of nutrients for the developing infant, but also contains both immunoglobulins and non-immunological factors that protect the infant from infection by various organisms. Human milk is also easily digested by the infant and is less likely to cause allergic reactions than is infant formula based on bovine milk.

Human milk differs from bovine milk as well as the milk of other mammalian species in various ways. Overall protein content and the kinds of protein differ between human and bovine milk. Four major bovine caseins have been identified. Bovine milk contains 2 α-caseins plus β- and χ-casein, but human milk contains only β- and χ-casein. Additionally, the amino acid sequences of human milk protein differ from that of other mammalian milk proteins.

Efforts have been made to develop infant milk formulas that have some of the advantageous properties of human milk and avoid the disadvantages associated with bovine milk based infant formulas such as allergic reactions and incomplete digestion by the infant. An intuitively desirable method to achieve this is to add to the formula some of the known constituents of human milk, including human milk proteins in their native form. The human caseins, which differ in amino acid sequence from their bovine and other mammalian counterparts, represent important substances which, if added in their native form to infant formula, would serve to enhance the nutritional value of the formula and reduce the inherent disadvantages of non-human milk proteins.

In addition to being a source of amino acids necessary for the synthesis of proteins required for the growth and development of infants, human milk is recognized as containing proteins, including casein, that have other important biological functions. β-casein is one of the most abundant milk proteins synthesized in the mammary gland. After post-translational modification in the Golgi apparatus, it is excreted as large calcium-dependent aggregates called micelles. β-casein is not a single entity, but is a heterogeneous group of phosphoproteins secreted during lactation in response to lactogenic hormones. The primary structure of human β-casein was determined by Greenberg et al.(*Journal of Biological Chemistry* 259:5132–5138, 1984). It was shown to be a phosphorylated protein with phosphorylation sites at specific seryl and threonyl residues located near the amino terminus. Comparison of human and bovine β-caseins showed 47% identity. The sequence of human χ-casein was determined by Brignon et al. (*Federation of European Biological Societies Letters* 188:48–54, 1985). Whereas β-casein is phosphorylated, χ-casein is glycosylated.

Several biological effects have been ascribed to human milk casein including: (1) enhancement of calcium absorption; (2) inhibition of angiotensin I-converting enzyme; (3) opioid agonism; (4) and immunostimulating and immunomodulating effects.

Human casein consists largely (>80%) of the β-form with a smaller amount in the χ-form (Greenberg et al., 1984). Native β-casein is a 25 kDa protein. In human milk, β-casein molecules show variable degrees of post-translational phosphorylation ranging from zero to five phosphate groups per polypeptide chain (Greenberg et al., 1984; Hansson et al., *Protein Expression and Purification* 4:373–381, 1993). Phosphate groups in the native protein are attached to serine and threonine residues located near the amino terminus (Greenberg et al., 1984).

Expression of exogenous genes in bacterial cells provides a useful method for producing recombinant eukaryotic proteins. However, bacteria, such as *E. coli*, are not capable of producing the post-translational modifications required by many eukaryotic proteins as they do not possess the endogenous enzymes necessary to do so. Therefore, eukaryotic proteins produced in *E. coli* lack the specific post-translational modifications which may occur within the eukaryotic cell, such as glycosylation, phosphorylation, acetylation, or amidation.

Prior to the development of appropriate cloning techniques, the phosphorylation of purified proteins by a kinase was done in vitro using chemical reagents. This process requires the protein substrate and the kinase enzyme to be purified and this is not efficient or cost-effective for commercial purposes. The in vitro process is also inefficient when it is desired to scale-up for commercialization. There is, therefore, a need to develop a method for genetically engineering microorganisms to phosphorylate a protein in vivo.

Canadian Patent Application No. 2,083,521 to Pawson et al. teaches a method of producing phosphorylated exogenous protein in host cells. The method of Pawson et al. requires two vectors to be introduced into a bacterial cell. One vector has a nucleotide sequence encoding an exogenous protein that is capable of being phosphorylated by the catalytic domain of a protein kinase. The other vector has a nucleotide sequence encoding the protein kinase catalytic domain. Both vectors are introduced into *E. coli* and production of the exogenous protein and the protein kinase catalytic domain is induced so that the exogenous protein is phosphorylated. The bacterial cells are then lysed and the exogenous phosphorylated protein is isolated using standard isolation techniques.

CA No. 2,083,521 does not suggest or disclose the method of the instant invention. The present inventors use a single vector expressing both the substrate and the kinase enzyme. The method of Pawson et al. requires the use of two vectors. The expression system disclosed herein results in specific phosphorylation of the exogenous protein as determined by antibody to phosphoserine, while the expression system of Pawson et al. results in non-specific phosphorylation of both host proteins and exogenous proteins. This would adversely affect the growth of host bacteria in scale-up efforts for industrial applications. The present invention, unlike that of Pawson et al., provides for high level production of a phosphorylated, recombinant protein suitable for commercial production.

Simcox et al., *Strategies in molecular biology* 7(3):68–69 (1994) constructed two *E. coli* strains that harbor a tyrosine kinase plasmid. These TK (tyrosine kinase) strains can be used for generating phosphorylated proteins when transformed with a plasmid containing sequences encoding a phosphorylation target domain or protein. Both *E. coli* strains carry an inducible tyrosine kinase gene. One strain, TKB1, is useful for expressing genes whose expression is directed by the T7 promoter. The system developed by Simcox et al. differs from the present invention in that it requires two constructs, i.e., a tyrosine kinase-containing plasmid and a plasmid vector containing a gene encoding a protein or domain to be phosphorylated.

In order to better understand the structure and function of human β-casein and to permit studies of factors that affect regulation of its synthesis and secretion, cDNA for this protein was cloned and sequenced (Lönnerdal et al., *Federation of European Biological Societies Letters* 269:153–156,1990), and human milk β-casein was produced in *Escherichia coli* and *Saccharomyces cerevisiae* (Hansson et al., 1993). Hansson et al. demonstrated that recombinant human β-casein was expressed in the yeast, *S. cerevisiae,* using the pYES 2.0 vector (Invitrogen Corp., San Diego, Calif.). Production levels were estimated to be approximately 10% of the production found in *E. coli.* However, recombinant β-casein obtained from *S. cerevisiae,* a eukaryotic cell that has endogenous enzymes capable of phosphorylating proteins, was phosphorylated, but the protein produced by *E. coli,* a prokaryotic cell that lacks the ability in its native state to phosphorylate, was non-phosphorylated. Subsequently, it was shown that recombinant human casein kinase II (rhCKII) produced in and purified from *E. coli* can phosphorylate protein substrates in vitro (Shi et al., *Proceeding of the National Academy of Sciences, USA* 91:2767–2771, 1994). One specific embodiment of the present invention uses a nucleotide sequence encoding a recombinant human casein kinase II in a single construct with nucleotide sequence encoding β-casein to transform *E. Coli* and produce phosphorylated β-casein. None of the prior art suggests or discloses a single vector containing a promoter followed by a nucleotide sequence encoding a protein followed by a nucleotide sequence encoding a kinase as is disclosed in the present invention.

SUMMARY OF THE INVENTION

There is disclosed herein a method for producing a modified recombinant protein in a host cell comprising preparing a single vector encoding both an exogenous protein and an enzyme capable of modifying the exogenous protein. Representative of exogenous proteins capable of being modified through the process of the present invention include but are not limited to human caseins, including β-casein, cell receptor proteins, fatty acylated proteins including palmitoylated proteins, mammalian muscle proteins, the gag polyproteins of retroviruses, and mammalian proteins targeted by retroviral src kinases. Transmembrane glycoproteins that acquire covalent palmitate after synthesis include the insulin, $β_2$-adrenergic and transferrin receptors. Proteins that function as cell surface receptors, tyrosine and serine/threonine kinases, their substrates, a phosphatase, G-proteins, and $Ca^{2+}$ are known to be fatty acylated. Representative of enzymes useful in the present invention because of their capacity to transfer functional groups to specific exogenous proteins in a host cell, include but are not limited to kinases, such as tyrosine kinases or casein kinase, transferases, such as mammalian and yeast palmitoyl transferases, and kinases coded for by the src gene of retroviruses. Representative of promoters useful in the present invention include inducible promoters such as T7, $λP_L$, $λP_R$, and Tac and constitutive promoters such as bla and spa. Representative of host cells capable of being transformed and then expressing the modified proteins, include but are not limited to the bacterial cells *E. coli* K-12 and *E. coli* B, Bacillus species, Lactobacillus species, and Streptococcus species and eukaryotic cells such as yeast cells or mammalian cells.

An exogenous protein is one that originates outside the organism that is producing it. The term is sometimes used in the relevant DNA cloning literature also to refer to the recombinant protein produced by the transformed recipient organism. Alternatively, an exogenous protein produced using DNA cloning techniques may be referred to as a recombinant protein. The terms will be used interchangeably herein since the distinction is frequently not made in the literature. However, in discussing the disclosed invention the word "recombinant" will be used to refer to the protein produced by the transformed organism, and "exogenous" will be used when referring to the native, non-recombinant protein or nucleotide sequence encoding the protein.

What is disclosed herein is a method for producing a modified recombinant protein in a host cell comprising the steps of preparing a single vector having a promoter sequence, an exogenous protein sequence, and a nucleotide sequence encoding an enzyme capable of modifying the exogenous protein; transforming the host cell with the vector; expressing the vector in the host cell whereby the produced enzyme modifies the produced recombinant protein; and isolating the produced, modified recombinant protein. Also disclosed herein in a more specific embodiment of the invention is a method for producing a phosphorylated recombinant protein in a host cell comprising the steps of preparing a single vector having a promoter sequence followed by a nucleotide sequence encoding an exogenous protein capable of being phosphorylated by a protein kinase, followed by a nucleotide sequence encoding a protein kinase capable of phosphorylating the exogenous protein; transforming the host cell with the vector; expressing the vector in the host cell whereby the produced protein kinase phosphorylates the produced recombinant protein; and isolating the phosphorylated protein.

More particularly the present inventors have developed a novel method for producing a modified recombinant human protein in bacterial expression systems wherein the resulting recombinant human protein has utility for the inhibition of attachment of *H. influenzae* to human cells and in the prevention and treatment of otitis media in human infants. Using a combination of two human casein kinase encoding sequences, expressing respectively the alpha and beta subunits of the kinase, they demonstrated the in vivo production of recombinant phosphorylated human β-casein in *E. coli.* The sequence coding for human casein kinase II was placed in tandem with the sequence coding for β-casein with the result that a significant portion of the recombinant β-casein produced in *E. coli* was phosphorylated as in human milk. The method of the present invention can also be used for in vivo specific glycosylation, amidation, or acetylation of recombinant proteins in transformed host cells or for the transfer of fatty acids to appropriate recombinant protein substrates in transformed host cells.

In a specific embodiment of the invention, a nucleotide sequence encoding a human casein kinase II (hCKII βα) is co-expressed in a single construct with a nucleotide sequence encoding a human β-casein in a bacterial expression system to achieve efficient in vivo phosphorylation of the appropriate serine and threonine residues of recombinant human β-casein. Experiments in which a nucleotide sequence encoding hCKII βα and a nucleotide sequence encoding human β-casein were co-expressed in *E. coli* using a single inducible expression vector demonstrated the ability of recombinant hCKII βα to phosphorylate recombinant β-casein in vivo. This was an unexpected, non-obvious result requiring experimentation and inventiveness. As was demonstrated by negative results obtained in early, control experiments the disclosed invention showed unexpected results. The method of the present invention produces useful and beneficial results which will permit the addition of beneficial human proteins to nutritional and pharmaceutical products.

Phosphorylated β-casein produced using the method of the invention is demonstrated to have the same bioactivity as native human β-casein as shown by its ability to inhibit adhesion of *H. influenzae* to human pharyngeal cells.

DETAILED DESCRIPTION OF THE INVENTION

The present invention relates to a method for producing a modified recombinant protein in a host cell. In a more specific embodiment the invention relates to a method for producing a phosphorylated human protein in a bacterial cell. The method comprises the steps of preparing a single vector having both a nucleotide sequence encoding an exogenous protein that is capable of being phosphorylated by a protein kinase and a nucleotide sequence encoding an appropriate protein kinase, expressing the vector in a host cell whereby the produced kinase phosphorylates the produced exogenous protein, and isolating the phosphorylated recombinant protein. The present inventors have made the unexpected discovery that placing the nucleotide sequence encoding the protein to be phosphorylated and the nucleotide sequence encoding the kinase in tandem in a single construct with a promoter results in high level and specific phosphorylation while eliminating the negative features associated with multiple vectors such as the need for antibiotic resistance genes to be used as markers. Use of the single construct system facilitates scaling up the procedure for industrial use. It is contemplated that the method of the invention will be useful in any host cell system that is capable of expressing the exogenous protein. Suitable host cells include both prokaryotes such as bacteria and eukaryotes such as yeast and animal cells.

In the preferred embodiment of the present invention the host cell is $E.$ $coli$. Nucleotide sequences encoding β-casein, in several different expression formats, were evaluated for expression of recombinant human β-casein in an $E.$ $coli$ strain. After a series of experiments, it was determined that recombinant human β-casein was efficiently phosphorylated when sequences encoding human β-casein were placed in a single construct with sequences encoding human casein kinase CKII βα. Efficiency of phosphorylation was not compromised when both genes were placed in tandem in one plasmid when compared with experimental systems in which sequences encoding the kinase and the β-casein were placed in two separate vectors.

Materials and Methods

The following materials and methods were used in the investigations described in Examples 1 to 5. Additional materials and/or methods are described for individual experiments when required. Materials and methods used in Example 6 are separately described.

Plasmids

Figure 1:
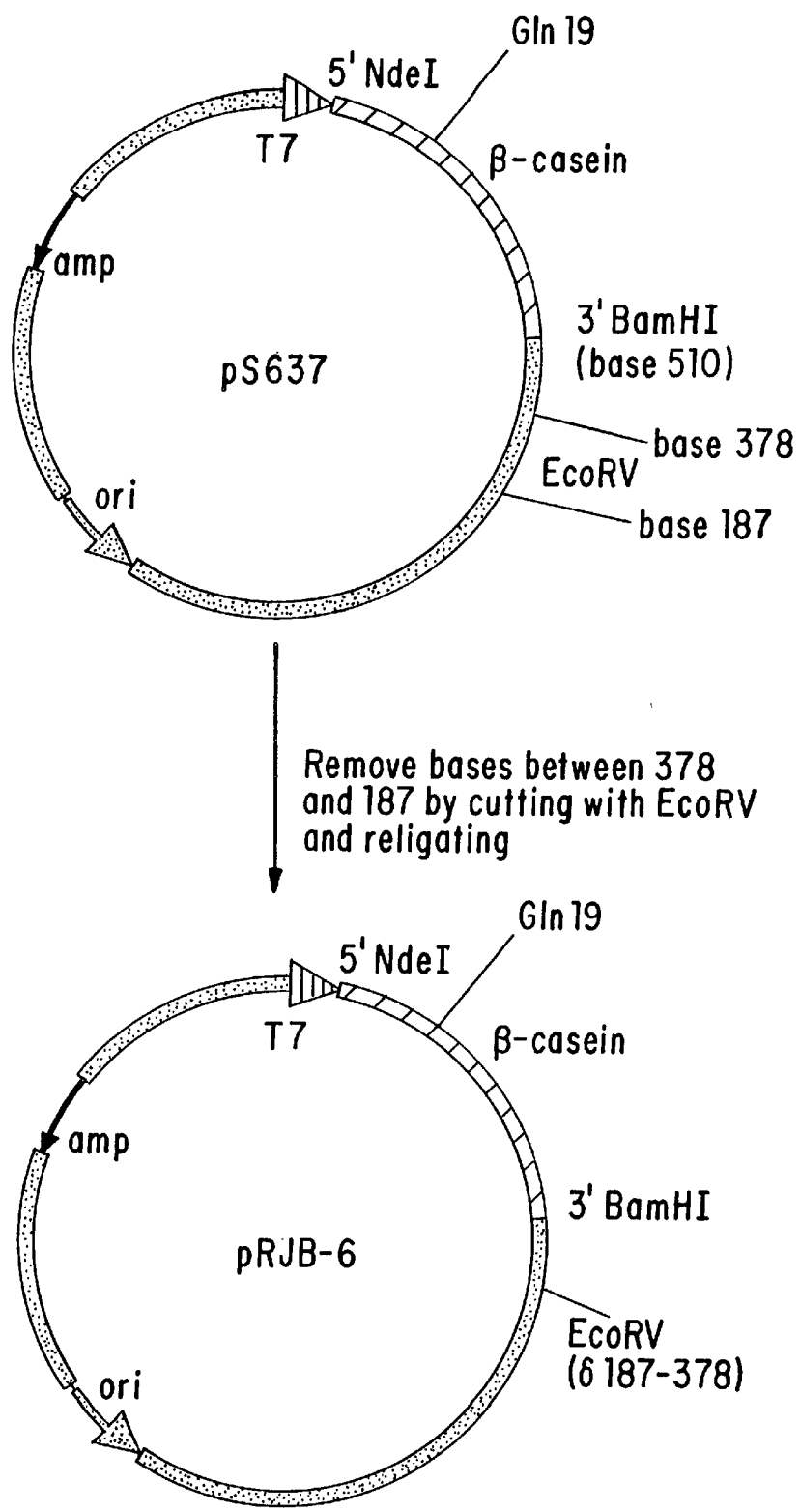
FIG. 1 shows physical maps of expression vectors pS637 and pRJB-6 constructed for inducible intracellular expression in *E. coli*. 191 base pairs were removed from pS637 to produce PRJB-6.

Plasmid construct pS637 shown in FIG. 1 is identical to pS26, constructed and described in Hansson et al., (1993), which is herein incorporated by reference, except that it encodes an additional amino acid, glutamine (Gln), at position 19. The original expression vector, pS26, was modified to create pS637 which produces a recombinant β-casein protein identical to the most abundant variant found in human populations.

Figure 2:
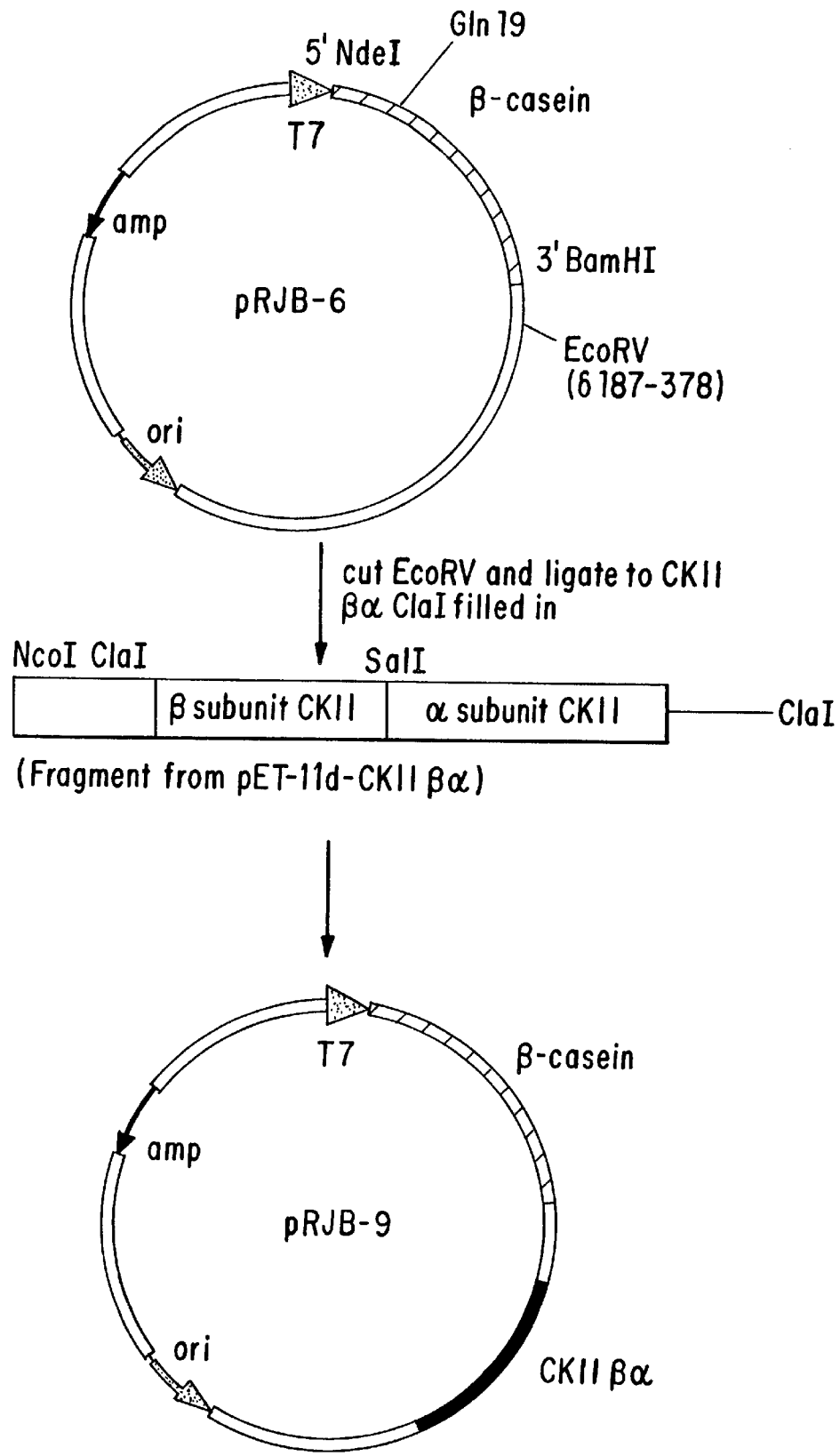
FIG. 2 shows physical maps of expression vectors pRJB-6 and pRJB-9 and illustrates how pRJB-6 was cut and ligated to CKII βα to form pRJB-9.

The construct pS637 was prepared for co-expression with the nucleotide sequence encoding casein kinase II (Shi et al., 1994), which is hereby incorporated by reference, by placing the nucleotide sequence encoding CKIIβα, which codes for two casein kinase subunits, β and α, as a cassette, downstream from the nucleotide sequence encoding β-casein. A three-cistron tandem expression vector pET-11d-CKII βα is a plasmid containing CKII βα that was generated by Shi et al. (1994). First, pS637 was cut at two sites downstream of the β-casein encoding sequence and relegated. A plasmid, pRJB-6, shown in FIG. 1, was isolated which had lost 191 bases between the two cut sites. The kinase CKII βα was prepared for insertion into pRJB-6. After insertion the resulting construct was designated pRJB-9, which is shown in FIG. 2. pRJB-9 is a single construct designed to mediate production of phosphorylated β-casein. pS637 was also modified to construct the plasmids pS750 and pRJB-7 which will be described in further detail below.

Host Cells

In the specific embodiment of the invention described below the host organism transformed by the described vectors was $E.$ $coli$. Other representative organisms that could be used with the method of the invention include Bacillus, Lactobacillus, and Streptococcus species.

Promoter

In the specific embodiment of the invention described below the T7 promoter was used. Other representative promoters that could be used with the method of the invention include the inducible promoters $\lambda P_L$ and $\lambda P_R$ and Tac and the constitutive promoters bla and spa.

Construction of Plasmids for Bacterial Expression: Detailed Methods

Expression Vector pS637

Expression vector pS637 differs from pS26, described in Hansson et al. (1993) as it contains a nucleotide triplet encoding the glutamine (Gln) amino acid residue at position 19 of the β-casein encoding sequence. This nucleotide sequence was isolated from a human cDNA variant that is more commonly found in human populations than is the sequence of pS26. Two synthetic oligonucleotides were synthesized for polymerase chain reaction (PCR) amplification. The synthetic oligonucleotides provide convenient restriction sites and incorporated codons for amino acids used preferentially by bacteria. The two oligonucleotides were designated SYM4174 (Seq.ID NO: 1) and SYM4175 (Seq.ID NO: 2) and have the following sequences:

SYM4174 5'-CGCTGCAGCATATGCGTGAAACCATC GAATC-3'
SYM4175 5'-CGGGATCCTGGTCCTCGTGTTTAACTT TTTCAACTTTCTGTTTGTATTCGGTGATCGATTC-3'

PCR amplification was performed as described in Ausubel et al., (eds.) $Current$ $Protocols$ $in$ $Molecular$ $Biology$ Vol.2, Supp.16, 15.0.3–15.1.17 (1991) and the amplified fragment was digested with PstI and AvaII to generate an 85 bp fragment. Plasmid pS21, described in Hansson et al. (1993) was digested with EcoRV and AccI and a 328 bp fragment was isolated by gel electrophoresis. The isolated fragment was purified from the agarose gel by electroelution and digested with AvaII. This resulted in a 197 bp AvaII/AccI fragment which was isolated. The 85 bp PstI/AvaII digested PCR-amplified fragment and the 197 bp AvaII/AccI were ligated into PstI/AccI digested pS25, a plasmid described in Hansson et al. The resulting plasmid construct was sequenced and designated pS636. A 644 bp NdeI and BamHI restriction fragment was isolated from pS636 and introduced into NdeI/BamHI digested vector pS26, a plasmid described in Hansson et al. The resulting expression vector was designated pS637.

Expression Vector pRJB-9

The pET-11d-CKII βα plasmid comprising the CKII βα encoding sequences generated by Shi et al. (1994) was prepared for co-expression with recombinant β-casein. First, 191 base pairs (bp) were removed from pS637 by cutting two EcoRI sites downstream from the β-casein encoding sequence and religating pS637. A plasmid, pRJB-6 (FIG. 1), was isolated, which had lost the 191 bp between the two sites and had retained a single EcoRV site located 132 bases away from the 3' end of the β-casein encoding sequence. The plasmid pET-11d-CKII βα, containing the CKII βα encoding sequence, was cut with ClaI and the site was filled in with Klenow enzyme (Stratagene, CA) to create blunt ends. The filled in, ClaI cut CKII encoding sequence was inserted into pRJB-6, downstream from the β-casein encoding sequence, and the resulting construct was designated pRJB-9 and is shown in FIG. 2.

Expression Vector pRJB-7

Figure 3:
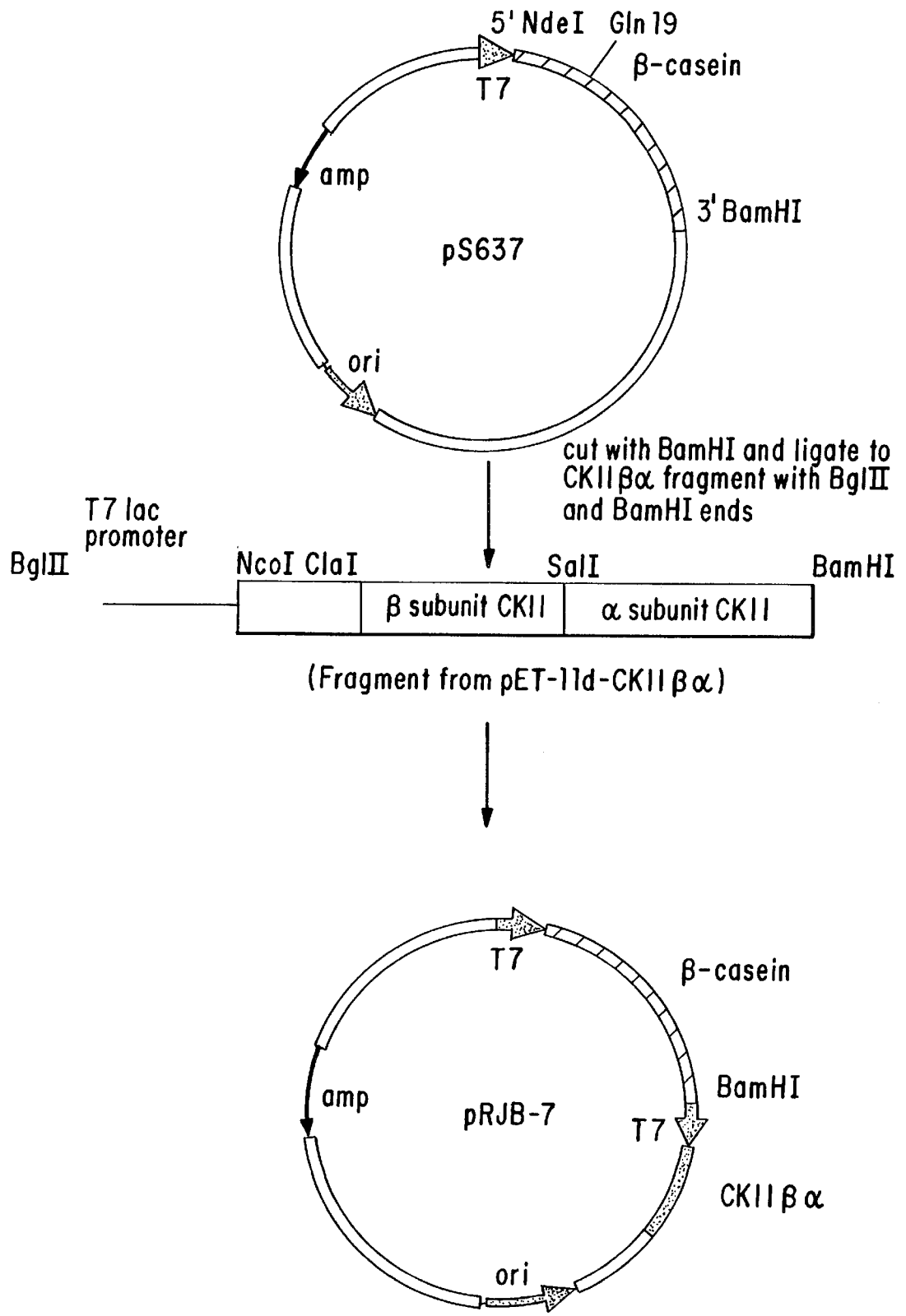
FIG. 3 shows physical maps of expression vectors pS637 and pRJB-7 and shows how pS637 was cut and ligated to CKII βα to form pRJB-7. pRJB-7 has T7 promoters in front of both the β-casein and casein kinase genes.

The construct pS637 was prepared for co-expression of recombinant β-casein and the CKII βα kinase by placing the CKII βα encoding sequence immediately after the β-casein encoding sequence. The CKII βα encoding sequence was placed as a BglII/BamH I fragment into the BamH I site of pS637 and designated pRJB-7. This fragment contained the T7 promoter from its original vector, pET-11D-CKII βα. Thus, as shown in FIG. 3, pRJB-7 contains two T7 promoters, one before the β-casein encoding sequence and one before the CKII βα encoding sequence.

Expression Vector pS750

Figure 4:
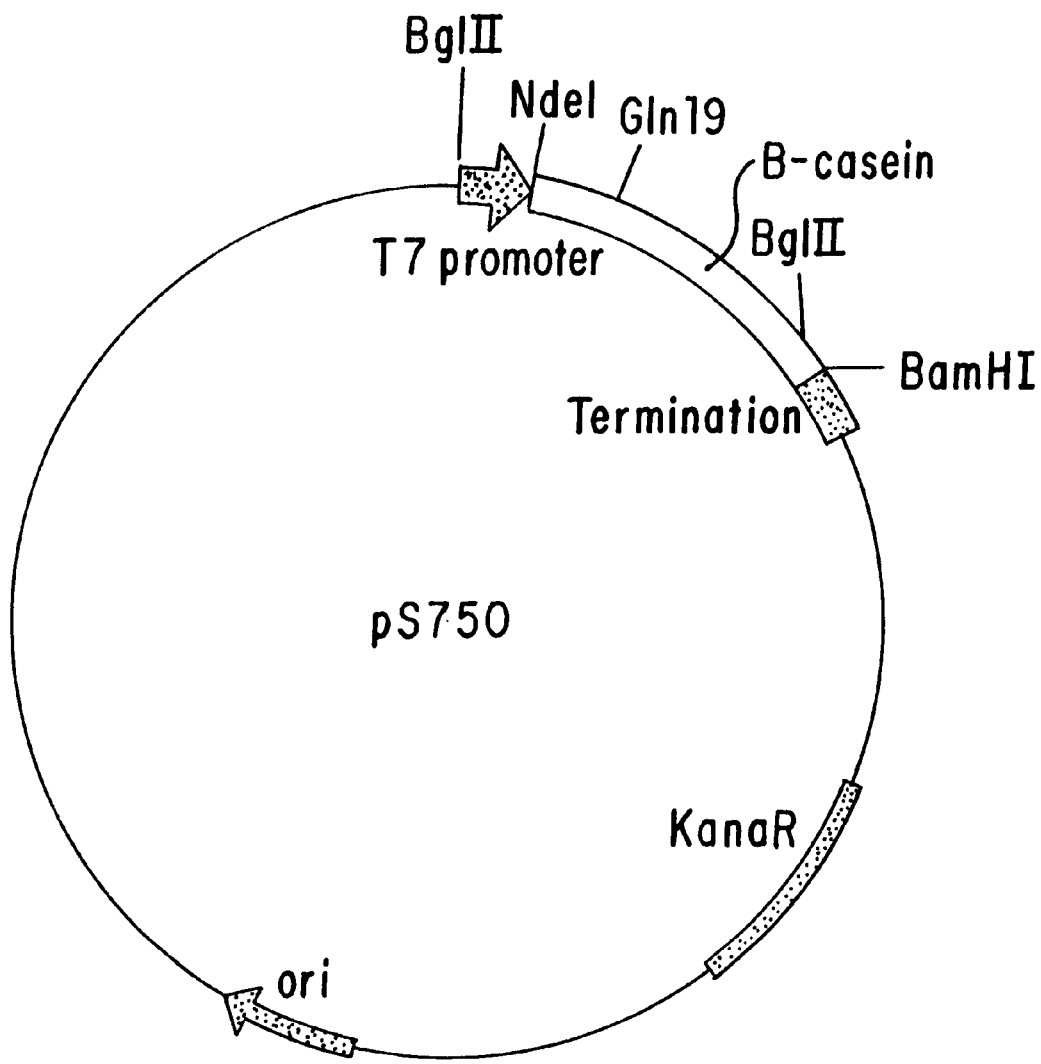
FIG. 4 shows the physical map of expression vector pS750, constructed for inducible expression and to mediate production of intracellularly localized protein in *E. coli*.

To change the selective marker from ampicillin resistance to kanamycin resistance, the plasmid pS637 was digested with PvuI and treated with T4 DNA polymerase to generate blunt ends. The linearized vector was isolated and ligated with a HincII kanamycin resistance genblock (Pharmacia, Uppsala, Sweden). The resulting expression vector was designated pS750 (FIG. 4).

Expression Vector for Recombinant Human Casein Kinase II

The expression vector pET-11d-CKII βα (Shi et al., 1994) was provided by Dr. C. Walsh of the Harvard Medical School, Boston, Mass.

Expression experiments were carried out as described by Studier et al. (*Methods in Enzymology* 185:60–89, 1990). Bacteria were grown in Luria Broth (LB medium) containing 50 μg/ml carbenicillin for pET-11d-CKII βα, the plasmid that contains a gene conferring resistance to carbenicillin, and 50 μg/ml kanamycin for the vector pS750, a plasmid containing a gene conferring resistance to kanamycin. The medium was supplemented with 30 μg/ml chloramphenicol when the strains containing the pLys plasmids, which confer resistance to chloramphenicol, were used. For induction of the T7 expression system, the cultures were grown to a density of approximately $OD_{600}$=0.5, and then 0.4 mM isopropyl β-D-thiogalactopyranoside (IPTG) was added. The cells were harvested about 90 minutes after induction.

Electrophoresis and Detection of Recombinant β-Casein

Cells were pelleted by centrifugation and the pellet from 1 ml of culture was dissolved in 100 μl of sample buffer, which contains Tris, glycerol, SDS, dithiothreotol (DTT), and bromophenol blue. The proteins were separated by SDS-PAGE as described in Laemmli (*Nature* 227:680–685, 1970). Gradient gels were cast and run in the discontinuous buffer system in a Protean (Bio-Rad, Richmond, Calif.) electrophoresis unit. Gels were stained as described in Laemmli. Immunoblotting was performed according to the specifications of the manufacturer (Bio-Rad).

Procedure for Isolation of Modified Protein

The modified protein can be isolated by any standard procedure known to those skilled in the art. Representative of such standard procedures is the following:

Cells are harvested and ruptured by standard mechanical or chemical procedures. Cells are then suspended in buffer, homogenized and centrifuged and the supernatant is discarded. The resulting insoluble pellet is resuspended and the supernatant is discarded. This results in a washed insoluble pellet that is suspended in 50 mM Tris and 6 M Urea at pH 8.2 and homogenized. β-casein supernatant I is removed resulting in an insoluble extract that is again suspended in 50 mM Tris and 6 M Urea at pH 8.2 and homogenized. β-casein supernatant II is removed and supernatants I and II are pooled. The remaining insoluble extract is discarded. The pooled supernatants are diluted 1:1 with 50 mM Tris and pH 8.2 and treated with 3 M Urea to extract β-casein. The final β-casein solution is obtained by dialyzing the Urea extract of β-casein against 50 mM ethanolamine and 100 mM NaCl at pH 9.5, centrifuging, and diluting in 50 mM ethanolamine, 100 mM NaCl at pH 9.5 to a protein concentration of 5 mg/ml. The pellet is discarded.

EXAMPLES

Examples 1 and 2 are provided to form a basis for the claimed invention, but are not part of the invention being claimed. The experiments described in Examples 1 and 2 show that production of recombinant β-casein is not adversely affected when bacteria are co-transformed with two vectors containing respectively a nucleotide sequence encoding β-casein and a nucleotide sequence encoding a casein kinase. They also demonstrate that recombinant phosphorylated β-casein can be produced using these two vectors in a bacterial system.

Example 3 demonstrates that the precise structure of the single plasmid was neither obvious nor expected, but that its construction required inventiveness and experimentation. Example 4 describes a system in which a single construct, containing a promoter and both the nucleotide sequence coding for the protein to be transcribed and phosphorylated and the nucleotide sequence coding for the kinase, was used to transform a bacterial strain. In Example 4, production of recombinant phosphorylated β-casein using a single plasmid was demonstrated. A single construct system for expression of extracellularly localized recombinant phosphorylated β-casein that is identical to human native β-casein is described in Example 5. Examples 4 and 5 are within the scope of the presently claimed invention. Example 6 shows a comparison of six phosphoforms of native human and recombinant human β-caseins made under the direction of the plasmid of the invention in their ability to inhibit adhesion of the bacterium *H. influenzae* to human pharyngeal cells.

Example 1

Production of β-casein in *E. coli* B:
Phosphorylation of Intracellularly Localized
Recombinant Met-β-casein: BL21(DE3) Strains To analyze the ability of recombinant human CKII (rhCKII) to phosphorylate recombinant β-casein in vivo in a bacterial expression system, experiments were performed in *E. coli* using two inducible expression vectors. The expression vector pS750 was transformed alone or in combination with expression vector pET-11d-CKII βα into the T7 host strains BL21(DE3), BL21(DE3)pLysS, and BL21 (DE3)pLysE. DE3 is a DNA fragment derived from a lambda phage containing a lacI repressor, a lacUV5 promoter which is inducible by isopropyl β-D-thiogalactopyranoside (IPTG), and a gene for T7 RNA polymerase. In the presence of the inducer, T7 RNA polymerase is produced resulting in transcription of the exogenous genes. Plasmid pLysS confers resistance to chloramphenicol and has little effect on growth rate and production of foreign protein. It contains a T7 lysozyme that increases stability of plasmids in *E. coli* and permits the cells to be lysed by freezing and thawing.

Figure 5:
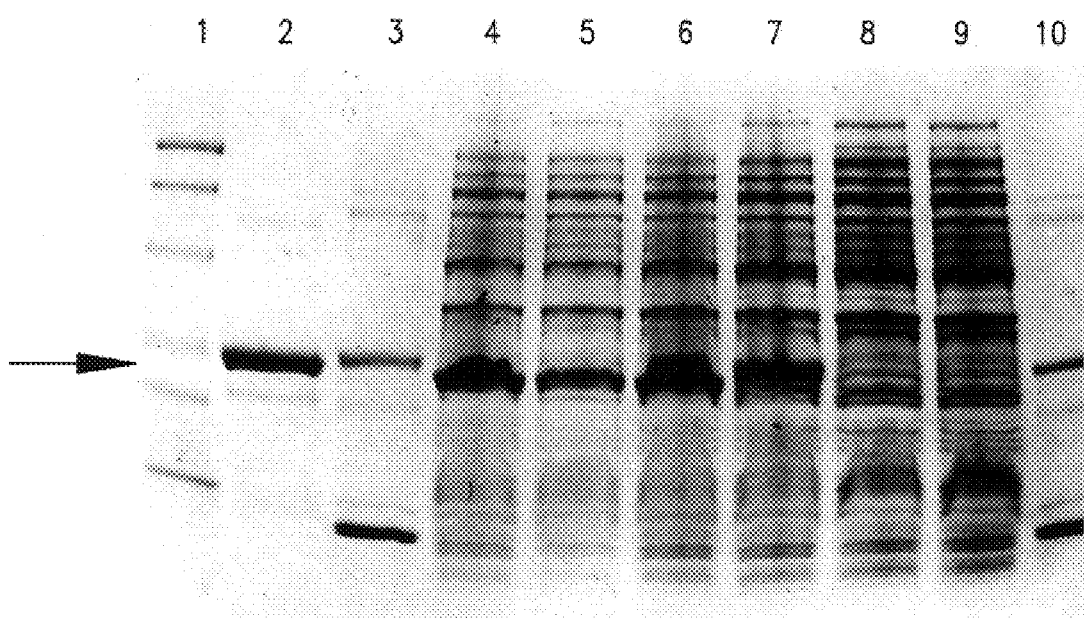
FIG. 5 shows SDS-PAGE of Met-β-casein produced in *E. coli* BL21 strains and stained with Coomassie Brilliant Blue using the vectors pS750 and pET-11d-CKII βα. The codon for methionine (Met) was placed in front of the β-casein encoding sequence in the construction of plasmid pS750 because in *E. coli* and other bacteria the synthesis of their proteins begins with the amino acid methionine. This enables the ribosome to recognize the starting point for growth of a polypeptide chain. Production of intracellular recombinant β-casein is possible only when Met is inserted before the encoding sequence for the protein to be produced. Lane 1: molecular weight marker (Bio-Rad prestained, relative molecular weights 106, 80, 49.5, 32.5, 27.5, 18.5 kDa); lane 2: non-phosphorylated recombinant β-casein; lane 3: 5P-β-casein; lane 4: pS750 induced with IPTG in BL21(DE3); lane 5: pS750/pET-11d-CKII βα induced with IPTG in BL21(DE3); lane 6: pS750 induced with IPTG in BL21 (DE3)pLysS; lane 7: pS750 /pET-11d-CKII βα induced with IPTG in BL21(DE3)pLysS; lane 8: pS750 induced with IPTG in BL21(DE3)pLysE; lane 9: pS750 /pET-11d-CKII βα induced with IPTG in BL21(DE3)pLysE cells; lane 10: native β-casein with five attached phosphate groups (5P-β-casein). The arrow indicates the β-casein band.
Figure 6:
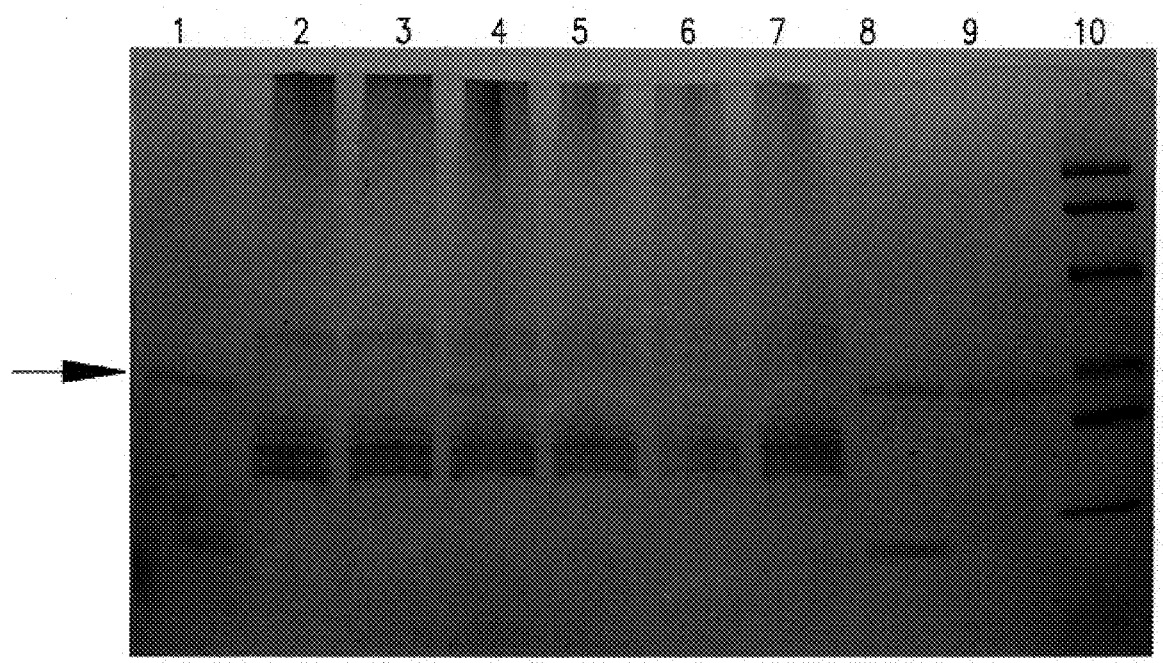
FIG. 6 shows SDS-PAGE of Met-β-casein produced in *E. coli* BL21 strains stained with Ethyl Stains-All using the vectors pS750 and pET-11d-CKII βα. Lane 1: native β-casein with five attached phosphate groups (5P-β-casein); lane 2: pS750 /pET-11d-CKII βα induced with IPTG in BL21(DE3)pLysE cells; lane 3: pS750 induced with IPTG in BL21(DE3)pLysE; lane 4: pS750 /pET-11d-CKII βα induced with IPTG in BL21(DE3)pLysS; lane 5: pS750 induced with IPTG in BL21(DE3)pLysS; lane 6: pS750 /pET-11d-CKII βα induced with IPTG in BL21(DE3); lane 7: pS750 induced with IPTG in BL21(DE3); lane 8: 5P-β-casein; lane 9: non-phosphorylated recombinant β-casein; lane 10: molecular weight marker (Bio-Rad prestained, relative molecular weights 106, 80, 49.5, 32.5, 27.5, 18.5 kDa). The arrow indicates the phosphorylated β-casein band, which is seen as a green band in the original photographs.

Results as seen in FIG. 5 indicate that high levels of recombinant human Met-β-casein were produced in *E. coli* and that the amount produced was not influenced by co-production of recombinant human CKII βα. After electrophoretic separation of the proteins and phosphate staining, CKII βα is seen to have phosphorylated recombinant human Met-β-casein in vivo. This is shown in FIG. 6 and demonstrates the ability to produce phosphorylated β-casein in a bacterial system using two vectors. This example is not within the scope of the claims and is provided to assist the examiner in understanding the inventive nature of the invention described in detail in Example 4.

Example 2

Figure 7:
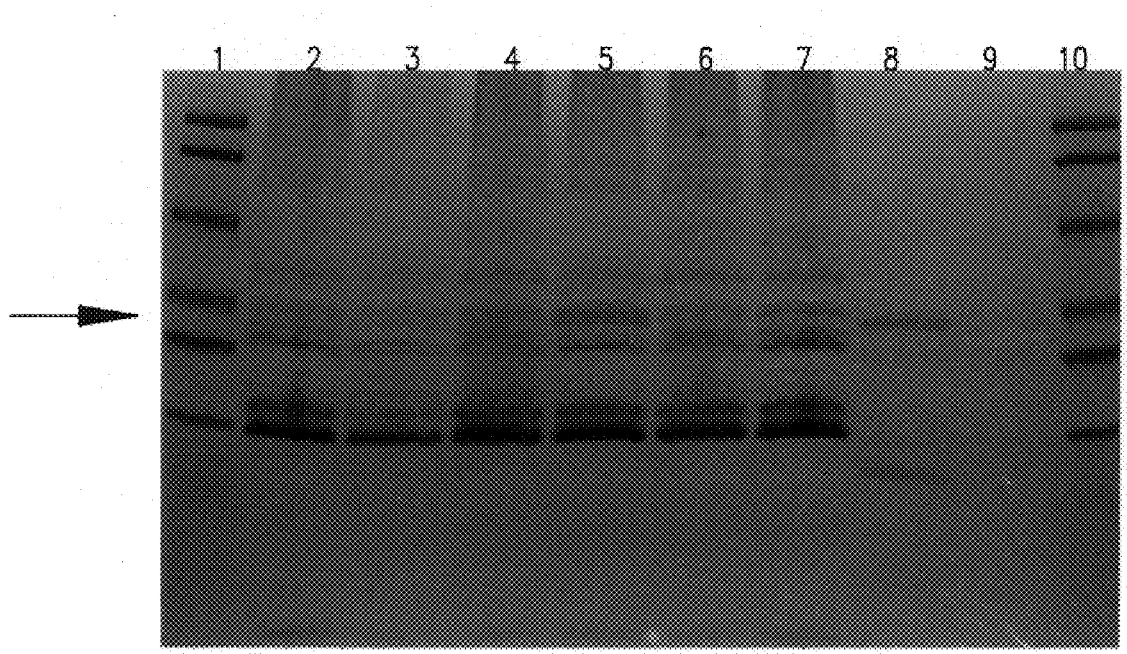
FIG. 7 shows SDS-PAGE of Met-β-casein produced in *E. coli* HMS174(DE3)pLysS stained with Ethyl Stains-All using the vectors pS750 and pET-11d-CKII. Lane 1: molecular weight marker (Bio Rad prestained); lane 2: pS750 uninduced; lane 3: pS750 induced with IPTG; lane 4: pS750 /pET-11d-CKII βα uninduced; lane 5: pS750 /pET-11d-CKII βα induced with IPTG; lane 6: pET-11d-CKII βα uninduced; lane 7: pET-11d-CKII βα induced with IPTG; lane 8: native 5P-β-casein; lane 9: recombinant β-casein; lane 10: molecular weight marker (Bio-Rad prestained, relative molecular weights 106, 80, 49.5, 32.5, 27.5, 18.5 kDa). The arrow indicates the phosphorylated β-casein band, which is seen as a green band in the original photographs.

Production of β-casein in E. coli K-12: Phosphorylation of Intracellularly Localized Recombinant Met-β-casein: HMS174(DE3) Strains E. coli K-12 strains HMS174(DE3), HMS174(DE3) pLysS, and HMS174(DE3)pLysE were evaluated as hosts for production of recombinant human Met-β-casein and were transformed with pS750. The most efficient production was achieved with HMS174(DE3)pLysS. Co-expression experiments using pS750 and pET-11d-CKII βα showed strong induction of recombinant human Met-β-casein production, which was independent of the presence of pET-11d-CKII βα. Phosphate staining (FIG. 7) showed efficient phosphorylation of Met-β-casein when co-produced in vivo with recombinant human CKII. This example, as was also the case for Example 1 is not within the scope of the claims, and is also provided to assist the examiner in understanding the inventive nature of the invention described in Example 4. A two plasmid system is inherently less desirable than the single plasmid system of the present invention as each of the plasmids must contain an antibiotic marker so that its presence in the host cells can be monitored during the fermentation process. This necessitates the use of two antibiotics in the growth medium and retards bacterial growth.

Example 3

Production of Human β-casein E. coli K-12: Construct pRJB-7 Containing Both a β-casein Encoding Sequence and CKII βα Encoding Sequences: T7 Promoter in Front of β-casein Encoding Sequence; T7 Promoter in Front of CKII βα Encoding Sequences The construct pRJB-7, containing the β-casein and the CKII βα genes each preceded by a T7 promoter, was transformed into E. coli K-12 host HMS174(DE3)LysS. The transformation and induction procedures followed were those of the Novagen pET system manual as described in Example 4.

Western Blot Analysis

Figure 8:
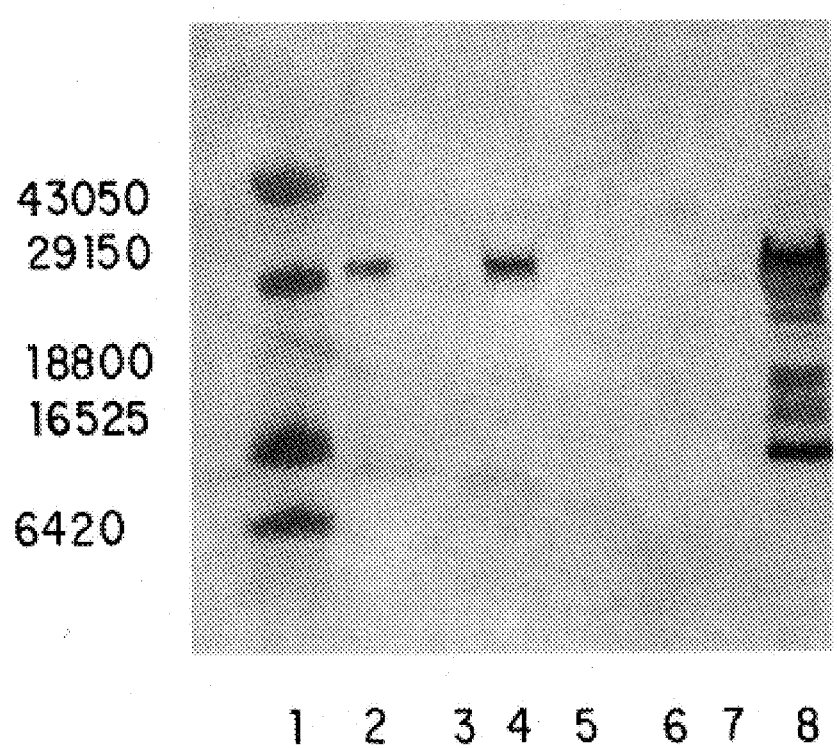
FIG. 8 shows a Western immunoblot analysis using antibody to human β-casein. Lane 1: molecular weight marker (Gibco BRL, relative molecular weights 43.1, 29.2, 18.8, 16.5, 6.4 kDa); lane 2: 50 ng native human β-casein; lane 3: uninduced HMS174(DE3)pLysS(pRJB-7); lane 4: induced HMS174(DE3)pLysS(pRJB-7); lane 5: uninduced HMS174(DE3)pLysS(pET-11d-CKII βα); lane 6: induced HMS174(DE3)pLysS(pET-11d-CKII βα); lane 7: uninduced HMS174(DE3)pLysS(pRJB-9); lane 8: induced HMS174(DE3)pLysS(pRJB-9).

Separation and transfer, blocking and antibody procedures are described in Example 4. FIG. 8 shows an immunoblot in which production of β-casein by E. coli HMS174 (DE3)LysS cells containing four different constructs is compared. Lysates from both induced and uninduced cell cultures are analyzed. Cells contain pET-11d-CKII βα (plasmid with CKII β and α encoding sequences), pRJB-9 (hybrid construct with both β-casein and CKII βα encoding sequences and T7 promoter in front of β-casein encoding sequence only), or pRJB-7 (hybrid construct with both β-casein and CKII βα encoding sequences and T7 promoters in front of both β-casein and CKII βα encoding sequences). Transformation of the bacteria with pRJB-7 resulted in severe reduction of bacterial growth. E. coli HMS174(DE3) LysS had approximately twice the doubling time as did the same strain transformed with pRJB-9, the construct with only one T7 promoter. The Western blot shown in FIG. 8 shows reduced production of recombinant β-casein by induced cells containing pRJB-7 when compared with cells containing pRJB-9. This is seen by comparing lane 4 (induced pRJB-7) with lane 8 (induced pRJB-9). Although both pRJB-7 and pRJB-9 are derived from pS637, only pRJB-9 produced amounts of β-casein equivalent to the parent construct. The presence of an additional T7 promoter before the CKII genes in the hybrid construct had the effect of both reducing cell growth and consequently reducing recombinant protein production.

Figure 9:
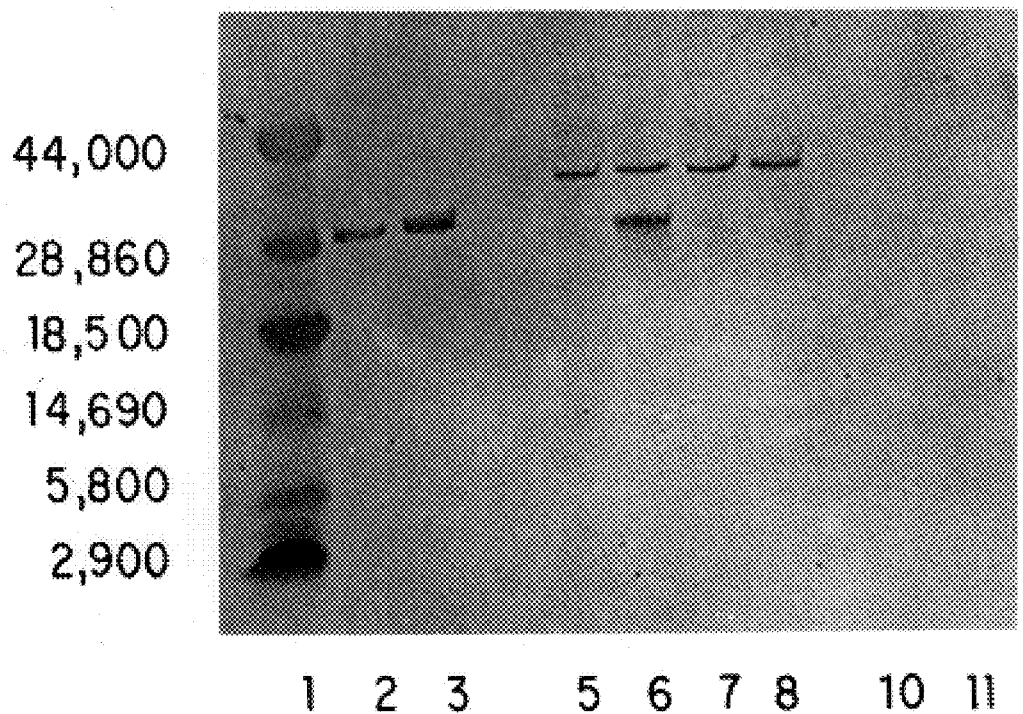
FIG. 9 shows a Western immunoblot analysis with antibody to phosphoserine. Lane 1: low molecular weight marker (Gibco BRL, relative molecular weights 44, 28.7, 18.5, 14.7, 5.8, 2.9 kDa); lane 2: 1 μg native human β-casein; lane 3: 2 μg native human β-casein; lane 5: induced HMS174(DE3)pLysS(pET-11d-CKII βα); lane 6: induced HMS174(DE3)pLysS(pRJB-9); lane 7: induced HMS174 (DE3)pLysS(pRJB-7); lane 8: induced HMS174(DE3) pLysS(pS637 ); lane 10: 1 μg recombinant human β-casein; lane 11: 2 μg recombinant human β-casein.

FIG. 9 shows a Western blot analysis in which the lysates were developed with phosphoserine antibody to detect phosphorylated protein. Induced E. coli HMS174(DE3)LysS cells containing pET-11d-CKII βα, pRJB-9 (hybrid construct with one T7 promoter), pRJB-7 (hybrid construct with two T7 promoters), or pS637 (contains β-casein encoding sequence but not CKII βα encoding sequence) were compared for production of phosphorylated recombinant β-casein. Phosphorylated β-casein was produced only in cells containing pRJB-9 (lane 6). No phosphorylated protein was detected in lane 7, which contains the lysate of cells containing pRJB-7.

Failure to detect phosphorylated protein in the construct with two T7 promoters indicates that both inventiveness and experimentation were required in order to develop the single construct system disclosed herein for expressing an appropriately modified recombinant protein in microorganisms. Although the experiment with two T7 promoters in a single construct containing the nucleotide sequence encoding a protein and the nucleotide sequence encoding a kinase gave a negative result, under different experimental conditions the use of more than one promoter sequence should not be excluded. Situations where it would be favorable to use two different promoters remain within the scope of the present invention.

Example 4

Production of Human β-casein in E. coli K-12: Construct pRJB-9 Containing Both β-casein Encoding Sequence and CKII βα Encoding Sequences The present invention uses a single construct expressing both the information for transferring functional groups to specific sites and the protein to be modified. In a specific embodiment of this invention the transferred functional group is phosphate. The transfer is accomplished by a kinase that is demonstrated to mediate phosphorylation of specific sites on recombinant human β-casein in vivo. This invention demonstrates that not only can human β-casein be specifically phosphorylated in vivo by E. coli, but that a single-construct with a promoter located before the sequence encoding β-casein and having the advantages of a single-construct system can successfully mediate this function.

Transformation Into E. coli K-12 HMS174(DE3)pLysS

The construct pRJB-9, containing the β-casein and CKII βα genes, was transformed into E. coli K-12 host HMS174 (DE3)LysS. The transformation procedure followed was that of the Novagen pET system manual (4th ed., TB No.55, June, 1994).

Induction of Expression

E. coli HMS174(DE3)LysS host cells containing plasmids pRJB-9 (FIG. 2), pS637 (FIG. 1), or pET-11d-CKII βα (Shi et al, 1994) were grown at 30° C. to a density of $OD_{600}$= 0.5–0.6. Culture samples were taken before and 6 hours after adding 1 mM of the inducer IPTG. Cells from two 1 ml aliquots were pelleted by centrifugation in a microcentrifuge. Cells were resuspended in sample loading buffer for gel electrophoresis after which 500 μl of the supernatants from each aliquot were collected. The spent culture medium was concentrated in a Microcon 10 spin filter (Amicon) for 35 minutes at 10,000×G. The retentate was collected after spinning for 3 minutes at 1,000×G and an equal amount of sample buffer at double concentration was added.

Western Blot Analysis

Cell lysates were separated on SDS-Polyacrylamide precast Gel (Integrated Separations System) with a 10–20% gradient and transferred to an Immobilon-P membrane (Millipore, Bedford, Mass.) with a semi-dry blotter. Gels were electroblotted at a constant current (0.8 mA/cm$^2$) for 45 minutes onto Immobilon PVDF filters (Millipore) using a Trans-Blot SD Transfer Cell (BioRad) The transfer buffer contained 48 mM Tris, 39 mM glycine, 1.3 mM SDS (sodium dodecyl sulfate) and 20% methanol. Prior to transfer, the filter was soaked first in methanol and then in transfer buffer. For Western blot analysis, the membrane was blocked in 3% bovine serum albumin and 0.2% Tween in TBS (25 mM Tris, 0.154 M NaCl, pH 7.4). Primary antibody to β-casein and alkaline phosphatase goat anti-rabbit antibody, the secondary antibody, were diluted 1:8000 in the blocking buffer. An additional antibody was used to detect phosphoserines. Blocking and antibody reactions were done at 25–26° C. in 2% gelatin containing amplification grade porcine skin (U.S. Biochemicals) in TBS for 2 hours. The blot was then rinsed with TBS for 30 minutes. Primary antibody, mouse monoclonal anti-phosphoserine (Sigma) was diluted 1:200 or 1:100 in the 2% gelatin blocker and incubated for two hours. The blot was rinsed twice in TBS for 5 minutes. The secondary antibody, goat anti-mouse alkaline phosphatase (Sigma), was diluted 1:4,000 in the gelatin blocker, incubated for one hour, and rinsed as before in TBS. Nitro blue tetrazolium and 5-bromo-4-chloro-3-indoyl phosphate were used as substrate for color development.

Figure 10:
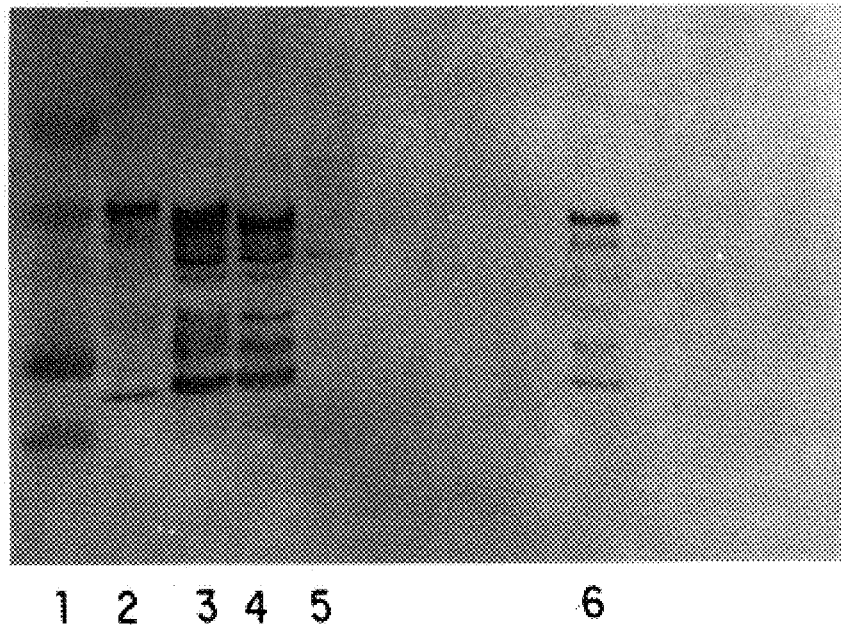
FIG. 10 shows an immunoblot analysis using antibody to human β-casein. Lane 1: molecular weight marker (Gibco BRL, relative molecular weights 44, 28.9, 18.5, 14.7, 5.8 kDa); lane 2: native human β-casein; lane 3: induced HMS174(DE3)pLysS(pRJB-9); lane 4: induced HMS174 (DE3)pLysS(pS637 ); lane 5: induced HMS174(DE3)pLysS (pET-11d-CKII βα); lane 6: recombinant human β-casein.

FIG. 10 shows an immunoblot in which production of β-casein by E. coli K-12 HMS174(DE3)LysS cells containing three different constructs is compared. Cells contain pS637 (plasmid with β-casein encoding sequence), pET11d-CKII βα (plasmid with CKII β and α encoding sequences), or pRJB-9 (hybrid construct with both β-casein and CKII βα encoding sequences). Comparison of lanes 3 and 4 shows that the hybrid construct, pRJB-9, is producing equivalent amounts of β-casein to pS637, from which it was derived and which does not contain the CKII βα encoding sequences. Both pRJB-9 and pS637 produced between 400–500 mg/L of β-casein in this host cell. This experiment shows that placing the β-casein encoding sequence in tandem with the encoding sequence for CKII βα does not significantly change production of β-casein.

Figure 11:
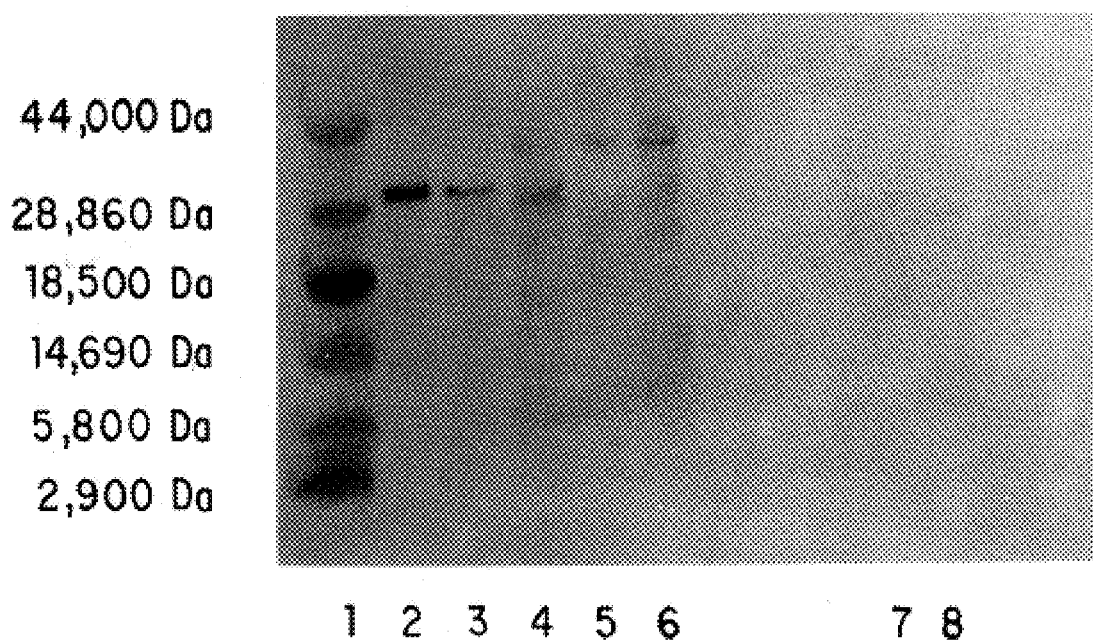
FIG. 11 shows an immunoblot analysis using antibody to phosphoserine. Lane 1: molecular weight marker (Gibco BRL, relative molecular weights 44, 28.9, 18.5, 14.7, 5.8, 2.9 kDa); lane 2: 1 μg native human β-casein; lane 3: 500 ng native human β-casein; lane 4: induced HMS174(DE3) pLysS(pRJB-9); lane 5: induced HMS174(DE3)pLysS (pS637); lane 6: induced HMS174(DE3)pLysS(pET-11d-CKII βα); lane 7: 1 μg recombinant human β-casein; lane 8: 500 ng recombinant human β-casein.

FIG. 11 shows a Western blot analysis in which the lysates were developed with phosphoserine antibody to detect phosphorylated protein. Increased quantities of native human β-casein and non-phosphorylated recombinant β-casein were tested in addition to the lysates of FIG. 8. No phosphorylation of bacterial proteins is seen in lane 6, which contains the lysate from the CKII βα plasmid, showing that phosphorylation is specific. The cell lysate in lane 4, containing pRJB-9 with the β-casein and CKII βα encoding sequences in tandem, shows a strong band cross-reacting with the antibody. The band of lane 4 has the same molecular weight as native human milk β-casein by electrophoretic analysis as seen in lanes 2 and 3. There was no cross-reactivity to recombinant, non-phosphorylated human β-casein, either purified as in lanes 7 and 8 or as expressed in vivo by pS637 in lane 5. This experiment demonstrates specific, high-level phosphorylation of intact, recombinant human β-casein in E. coli K-12 in a bacterial system using a single construct.

Example 5

Production of β-casein in E. coli K-12: Phosphorylation of Extracellularly Localized Recombinant β-casein: Construct Containing E. coli Leader Sequence, Promoter, β-casein Encoding Sequence, DET-11d-CKII βα

In this example we disclose the construction of a single plasmid that is used to transform E. coli K-12 and mediate production of extracellularly localized phosphorylated β-casein. To create a single construct designed for secretion of phosphorylated protein to the periplasmic space of a bacterial cell, the β-casein encoding sequence is put into an expression vector containing a leader sequence that directs protein transport to the periplasm. A polymerase chain reaction (PCR) is performed using the clone resulting from these procedures as the target DNA. The following primers synthesized at Midland Certified Reagent Co. (Midland, Tex.). can be used in the PCR, RO-4: 5'-TGT AAA ACG GCC ACT-3' (Seq.ID No: 3) and RO-29: 5'-GGG GAT CCG TA<u>C</u> GCG TGA AAC-3' (Seq.ID No: 4) The base underlined in RO-29 incorporates a single base change to create an MluI site at the end of the β-casein encoding sequence in order to eliminate the bacterial initiation codon, methionine, for protein synthesis. This is done so that the resulting protein will have an amino acid sequence identical to that of human β-casein. The PCR fragment is then purified. The 3' end of the encoding sequence, which is not modified, is cut with BamH I. This fragment, containing a 5' blunt end and 3' BamH I end, is cloned in the expression vector pET-26b (Novagen, Madison, Wis.), which contains a T7 promoter, and cut at the blunt end with MscI and with BamH I. The construct described here contains the T7 promoter, but other promoter sequences could be used. The CKII βα encoding sequence is inserted as described above for pRJB-9. Expression is induced and Western blot analysis is performed according to the procedures described in Example 4.

A Western blot is performed to identify a protein, isolated from the periplasmic space of the bacterial cells, that cross-reacts with antibody to phosphoserine and migrates similarly to native β-casein. This experiment demonstrates phosphorylation of recombinant human β-casein encoded by a sequence fused to a heterologous translational start and signal sequence, this sequence being preceded by a promoter sequence, and the sequence to be phosphorylated being located in a plasmid containing a kinase encoding sequence such as CKII βα. Production of extracellularly localized phosphorylated protein has not been previously disclosed either in a one-vector or a two-vector system.

The advantage of extracellular over intracellular localization of the produced phosphorylated protein lies in the ease of its purification. The periplasmic space of bacterial cells contains less extraneous matter than the interior of the cell so that isolation of the purified protein is expedited. This is particularly advantageous during commercial production.

Example 6

Comparison of Anti-Adhesion Bioactivity of Native and Recombinant Human β-Casein Haemophilus are small, gram-negative bacilli with a lipopolysaccharide-protein cell wall and are obligate parasites present on the mucous membranes of humans and animal species. The surface of many but not all strains of *Haemophilus influenzae* is covered with a polysaccharide capsule. Nonencapsulated, nontypeable *H. influenzae* strains colonize the upper respiratory tract in most individuals within the first few months of life and is the species most commonly associated with several diseases including otitis media and sinusitis. (Murray et al., *Medical Microbiology*, 2d ed., p.260, 1994). They can also exacerbate chronic bronchitis.

An assay was performed to compare the activity of native human β-casein with recombinant human β-casein synthesized in cells containing pRJB-9 in inhibiting adherence of *H. influenzae* to human pharynx cells. Comparisons were made between proteins phosphorylated with 0 to 5 phosphates.

Cells and Bacterial Strains

Detroit 562 human pharynx carcinoma cells (DT 562) were obtained from the American Type Culture Collection (Rockville, Md.). The *H. influenzae* nontypeable bacterial strain was obtained from Dr. Lauren Bakaletz at the Ohio State University.

Cell Culture

DT 562 cells seeded into 96-well plates (Costar, Cambridge, Mass.) at a density of 20,000–25,000 cells per well were cultured in Dulbeccos's Modified Eagle Medium (GIBCO, Grand Island, N.Y.) supplemented with 10% fetal bovine serum (FBS) (Hyclone, Logan, Utah). Cells were incubated in a humidified atmosphere of 95% air and 5% carbon dioxide at 37° C. Experiments were conducted when cells were at least 90% confluent. Plates containing cells were washed three times with 200 μL of Hanks Balanced Salt Solution (HBSS) (GIBCO) to remove serum proteins before the addition of bacteria.

Native Human β-casein

β-casein isolated from human milk was purchased from Symbicom AB, P.O. Box 1451, S-902 24 Umea, Sweden.

Separation of Phosphoforms

Cells were harvested by centrifugation at 7000×g for 10 minutes at 40° C. Supernatant was removed and the pelleted cells were subjected to the freeze/thaw method described in Johnson et al. (Bio/Technology, Dec. 12, 1994, pp.1357–1360) to release the recombinant β-casein. After filtration through a 0.45 μ membrane, samples containing β-casein were loaded onto an anion exchange column (Mono Q 10/10, Pharmacia Biotech, Uppsala, Sweden). Various phosphoforms were resolved on a linear gradient of 0 to 0.5 M NaCl in 20 mM ethanolamine, 6 M urea, at pH 9.5 over a period of 50 minutes.

Different phosphoforms of recombinant β-casein were identified by comparison of their elution times with those of purified native human milk β-casein.

Radiolabeling of Bacteria

*H. influenzae* were streaked onto chocolate agar plates from frozen aliquots of a low passage number and incubated at 37° C. in a humidified atmosphere of 95% air and 5% carbon dioxide for 18 hours to obtain log phase cultures. Bacteria harvested in phosphate buffered saline (PBS) supplemented with 0.05% bovine serum albumin ((BSA) were centrifuged and resuspended in a volume of PBS/BSA yielding an optical density of 2.4 at a wave length of 600 nm ($OD_{600}$). $^{111}$Indium-oxine ($^{111}$In) (Amersham, Arlington Heights, Ill.) was used to radiolabel the bacteria. 50 μCi of the $^{111}$In solution was added to 2.5 ml of the bacterial suspension and incubated for 20 minutes at 37° C. The radiolabeled bacteria were washed twice with 10 ml HBSS to removed unbound $^{111}$In and resusupended in 5 ml HBSS supplemented with 30 nM HEPES buffer (N-2-hydroxyethylpeperazine-N'-2-ethane sulfonic acid). 25 μL of the $^{111}$In labeled bacterial suspension were preincubated with 25 μL of the test agent in a polypropylene 96-well plate for 15 minutes at 37° C. to allow binding of the agent to the bacteria.

Quantitation of Adhesion

25 μL of the preincubation mixture containing radiolabeled bacteria and either native human or recombinant β-casein was pipetted into each well of the assay plate containing DT 562 cells. The assay plate was incubated for 20 minutes at 37° C. to allow adhesion of the bacteria to the cell monolayer. Nonadhering bacteria were removed by washing the plate three times with HBSS. The assay was terminated by the addition of 100 μL of 0.05 N sodium hydroxide to disrupt the cell monolayer and the adhering *H. influenzae*. The contents of each well was placed in a Cobra polypropylene tube and counted on a Cobra gamma counter (Packard, Meriden, Conn.). Results were calculated by averaging the results of four replicates. Results are presented as the percent inhibition of bacterial adhesion with native human or recombinant (pRJB-9 ) β-casein at 6 different phosphorylation levels when compared to bacterial attachment in control wells containing no test agent.

Results

Anti-adhesion activity is only seen consistently when β-casein is phosphorylated with 3, 4, or 5 phosphate groups. At lower levels of phosphorylation little or no anti-adhesion was observed with either native or recombinant β-casein. However, at higher phosphoforms when β-casein had 3, 4, or 5 phosphates there was essentially no difference between the anti-adhesion bioactivity of native or recombinant (pRJB-9) human β-caseins. These results show that the bioactivity of β-casein in inhibiting adhesion of *H. influenzae* to human pharyngeal cells depends upon the level of phosphorylation. Unphosphorylated or minimally phosphorylated β-casein is ineffective. Attachment of 3, 4, or 5 phosphate groups is required for inhibition of adhesion of *H. influenze* to human pharyngeal cells. Results also demonstrate that phosphorylated recombinant β-casein made with the plasmid of the invention is as effective as native human β-casein in inhibiting adhesion of *H. influenzae*. These results are summarized in Table 1.

TABLE 1

ANTI-ADHESION BIOACTIVITY OF NATIVE AND RECOMBINANT (pRJB-9) HUMAN BETA-CASEINS

| Native Hβ | | | Recombinant Hβ | | |
|---|---|---|---|---|---|
| Phosphoform | Test Concentration (mg/ml) | Adhesion Inhibition | Phosphoform | Test Concentration (mg/ml) | Adhesion Inhibition |
| 0P | 1.00 | 15% | 0P | 0.40 | -2% |
| 1P | 1.00 | 0% | 1P | 0.76 | -4% |
| 2P | 1.00 | -11% | 2P | 0.76 | 35% |
| 3P | 1.00 | 47% | 3P | 0.76 | 43% |
| 4P | 1.00 | 52% | 4P | 0.76 | 51% |
| 5P | 1.00 | 50% | 5P | 0.76 | 48% |

*H. influenzae* has been identified as a causative factor for otitis media (Murray et al., 1994). Since it has been demonstrated in the experiments described above that recombinant human β-casein phosphorylated in at least three sites under the direction of the plasmid of the invention inhibits adhesion of *H. influenzae* to human cells, it is concluded that phosphorylated recombinant human β-casein, as described above, may be used in the prevention and treatment of otitis media in humans, particularly in human infants.

Therapeutic effects may be provided by enterally feeding or ingesting an enteral liquid nutritional product, such as infant formula, comprising a therapeutically effective amount of the phosphorylated recombinant human β-casein with 3 or more phosphate groups disclosed herein. It is understood that a liquid nutritional product, such as infant formula, may further contain at least one other protein from a mammalian milk, such as human milk, cow's milk, or goat's milk, and/or at least one other protein from a vegetable source such as soybeans or rice. The attachment of *H. influenzae* to human oropharyngeal cells may also be inhibited by administering via a nasal passageway, or as a throat spray, a formulation containing a therapeutically effective amount of phosphorylated recombinant human β-casein. Such a nasally administered formulation may be in the form of either drops or a spray. Administration of enteral, throat spray and nasal products is believed to be effective because the interaction of human β-casein is believed to occur by direct contact in the nasopharynx rather than after ingestion and digestion of the β-casein.

This invention will allow commercial-scale production of phosphorylated, recombinant mammalian proteins in microorganisms. The method of the invention can be used to produce recombinant exogenous proteins, including but not limited to, recombinant human β-casein, in large quantities. Phosphorylation of β-casein in a bioreactor makes possible large-scale synthesis in a fermentor of recombinant β-casein that is equivalent to native human β-casein. This will facilitate the production of infant formula containing human β-casein in its native phosphorylated state. The method of the invention can also be used for phosphorylation of cell proteins, including receptors which are regulated by phosphorylation and dephosphorylation and thereby act as signals in cell metabolism. The invention provides a cost-effective method of phosphorylating peptide receptors and will be useful in the manufacture of pharmaceutical drugs.

The single plasmid system is preferable to a two-plasmid system for industrial production of fermented proteins such as recombinant, phosphorylated human β-casein. Large-scale production of recombinant protein without the selective pressure provided by antibiotics in the growth medium results in plasmid loss during the fermentation process since the cells containing the plasmids would have no selective advantage over those that contained only one or no plasmids, but would be burdened by the presence of the plasmids resulting in slower growth. However, use of multiple antibiotics to provide the selective pressure necessary to maintain both plasmids in the bacteria during fermentation frequently retards bacterial growth and results in lower yield of the desired recombinant product. Therefore, for industrial purposes the single-plasmid system disclosed herein is greatly preferable to previously disclosed two-plasmid systems.

Phosphorylated recombinant human β-casein with 3 to 5 phosphate groups can be incorporated into any standard or specialized enteral liquid nutritional product including but not limited to infant formulas containing protein from non-human mammalian milk such as bovine or goat milk or protein from vegetable sources such as soybeans or rice, as well as other beverages consumed by young children. A product incorporating phosphorylated recombinant human β-casein having 3 to 5 phosphate groups has utility for the inhibition of attachment of *H. influenzae* to human cells and in the treatment and prevention of otitis media in human infants.

The discovery disclosed herein of a novel method for producing recombinant, phosphorylated human β-casein, with characteristics similar or identical to that of native human β-casein, makes feasible the addition of this protein to infant formula so as to render it more similar to human milk with consequential benefits to developing infants. The disclosure of a method for producing recombinant, modified human proteins in a bacterial system also makes feasible the addition of the human proteins to other food and pharmaceutical products.

Although specific preferred embodiments of the invention have been described above with reference to the accompanying experiments and drawings, it will be apparent that the invention is not limited to those precise embodiments and that many modifications and variations could be effected by one skilled in the art without departing from the spirit or scope of the invention as defined in the appended claims.

What is claimed is:

1. A composition comprising non-human mammalian milk, wherein said milk comprises recombinant phosphorylated human β-casein having at least two phosphate groups.

2. The composition of claim 1 wherein said recombinant phosphorylated human β-casein has been synthesized under the direction of a plasmid comprising: a) a promoter operably linked nucleotide sequence being followed by c) a nucleotide sequence encoding an enzyme which specifically phosphorylates human β-casein such that resulting phosphorylated recombinant human β-casein has at least two phosphate groups, wherein said nucleotide sequence encoding said enzyme and said nucleotide sequence encoding said human β-casein are regulated by said promoter.

3. The composition of claim 2, wherein said promoter is an inducible promoter selected from the group consisting of T7, $\lambda P_L$, $\lambda P_R$, and Tac.

4. The composition of claim 2, wherein said promoter is a constitutive promoter selected from the group consisting of bla and spa.

5. The composition of claim 2, wherein said enzyme is human casein kinase II (CKII).

6. The composition of claim 1, wherein said composition is a nutritional or pharmaceutical composition.

7. A composition comprising recombinant phosphorylated human β-casein having at least two phosphate groups and at least one non-human mammalian protein.

8. The composition of claim 7 wherein said composition comprises recombinant phosphorylated human β-casein having at least three phosphate groups.

9. The composition of claim 8 wherein said composition comprises recombinant phosphorylated human β-casein having at least four phosphate groups.

10. The composition of claim 9 wherein said composition comprises recombinant phosphorylated human β-casein having at least five phosphate groups.

11. The composition of claim 1 wherein said recombinant phosphorylated human β-casein has at least three phosphate groups.

12. The composition of claim 11 wherein said recombinant phosphorylated human β-casein has at least four phosphate groups.

13. The composition of claim 12 wherein said recombinant phosphorylated human β-casein has at least five phosphate groups.

\* \* \* \* \*